United States Patent [19]

Kami et al.

[11] Patent Number: 5,351,677
[45] Date of Patent: Oct. 4, 1994

[54] MEDICAL SYSTEM HAVING OBJECT INFORMATION REPRODUCTION MEANS FOR PALPATION

[75] Inventors: Kuniaki Kami; Hideyuki Adachi, both of Hachioji; Koichi Umeyama, Kasukabe; Yoshihiro Kosaka, Hachioji; Seiji Yamaguchi, Hachioji; Eiichi Fuse, Hachioji; Michio Sato, Hino; Masakazu Nakamura, Hachioji; Yasundo Tanaka, Urawa; Takashi Fukaya, Hachioji; Kiyotaka Matsuno, Hachioji; Katsuya Suzuki, Hachioji, all of Japan

[73] Assignee: Olympus Optical Co., Ltd., Tokyo, Japan

[21] Appl. No.: 868,642

[22] Filed: Apr. 15, 1992

[30] Foreign Application Priority Data

Apr. 24, 1991 [JP] Japan .................. 3-094459

[51] Int. Cl.⁵ .................. A61B 1/06; G06F 15/42; H04N 7/18
[52] U.S. Cl. .................. 128/6; 364/413.13; 348/45; 128/4
[58] Field of Search .................. 128/6, 4, 774, 739, 128/736, 664, 665, 715, 662.06, 915, 905, 897, 899; 358/98; 73/865.7, 865.8, 81, 79; 434/113, 114, 275; 364/419, 413.13, 413.18, 413.19; 340/709, 710, 825.19; 250/560; 395/153, 161; 318/628; 345/156, 163, 160, 65; 341/20, 27

[56] References Cited

U.S. PATENT DOCUMENTS

| | | | |
|---|---|---|---|
| 4,881,900 | 11/1989 | Matsuoka et al. | 434/113 |
| 4,900,144 | 2/1990 | Kobayashi | 250/560 |
| 4,935,810 | 6/1990 | Nonami et al. | 358/98 |
| 4,982,725 | 1/1991 | Hibino et al. | 128/4 |
| 4,986,262 | 1/1991 | Saito | 128/6 |
| 5,091,865 | 2/1992 | Yamada et al. | 395/153 |
| 5,186,629 | 2/1993 | Rohen | 434/114 |

FOREIGN PATENT DOCUMENTS

| | | | |
|---|---|---|---|
| 61-65903 | 5/1986 | Japan . | |
| 61-87530 | 5/1986 | Japan . | |
| 61-92650 | 5/1986 | Japan . | |
| 62-166312 | 7/1987 | Japan . | |
| 0189583 | 7/1987 | Japan | 73/865.7 |
| 1-221134 | 9/1989 | Japan . | |
| 2-216403 | 8/1990 | Japan . | |

Primary Examiner—Richard J. Apley
Assistant Examiner—John P. Leubecker
Attorney, Agent, or Firm—Armstrong, Westerman, Hattori, McLeland & Naughton

[57] ABSTRACT

A medical system has a detecting device for detecting three dimensional image information about a living body, a signal processing circuit for processing the image signal transmitted from the detecting device, and an object information reproduction device. The object information reproduction device comprises a movable displacement element which is touched by the operator and acts according to the output from the signal processing circuit so as to cause the operator to tactually sense information about the object. Thus, the operator is able to recognize the degree of unevenness in a tactile manner by touching the displacement element. Other embodiments include means for sensing and reproducing hardness and temperature of the object.

9 Claims, 13 Drawing Sheets

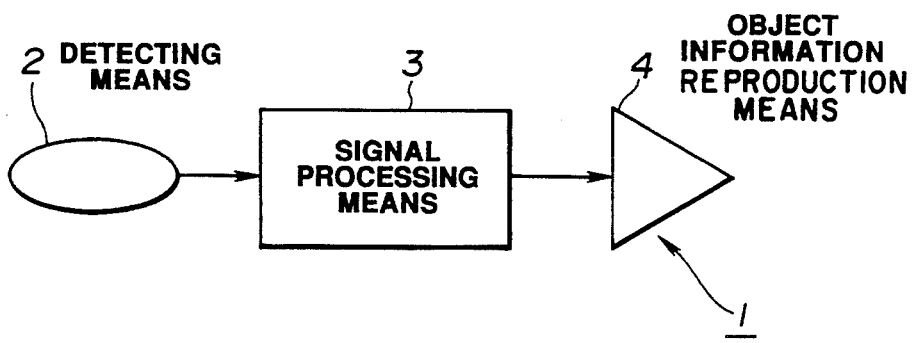
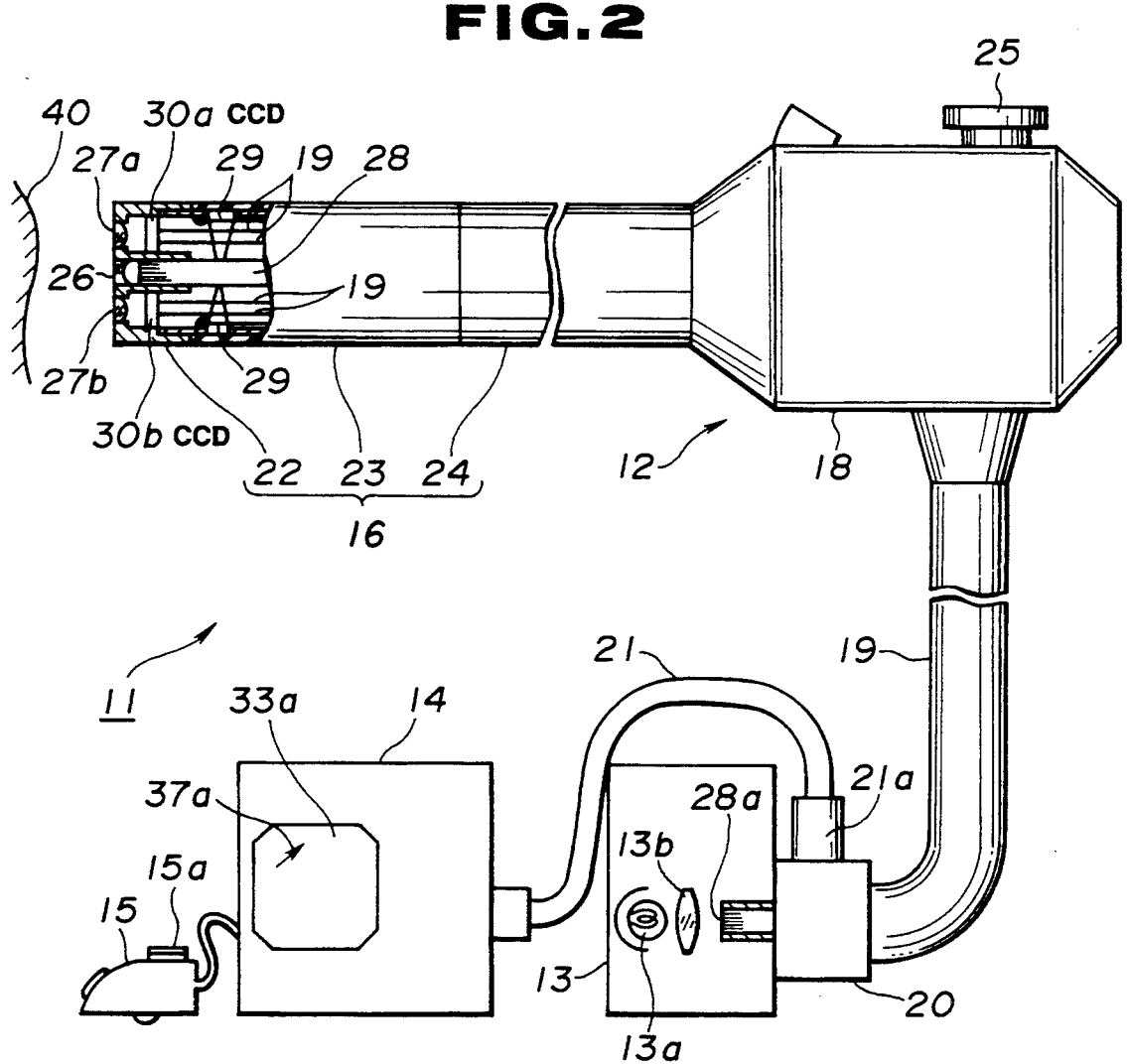

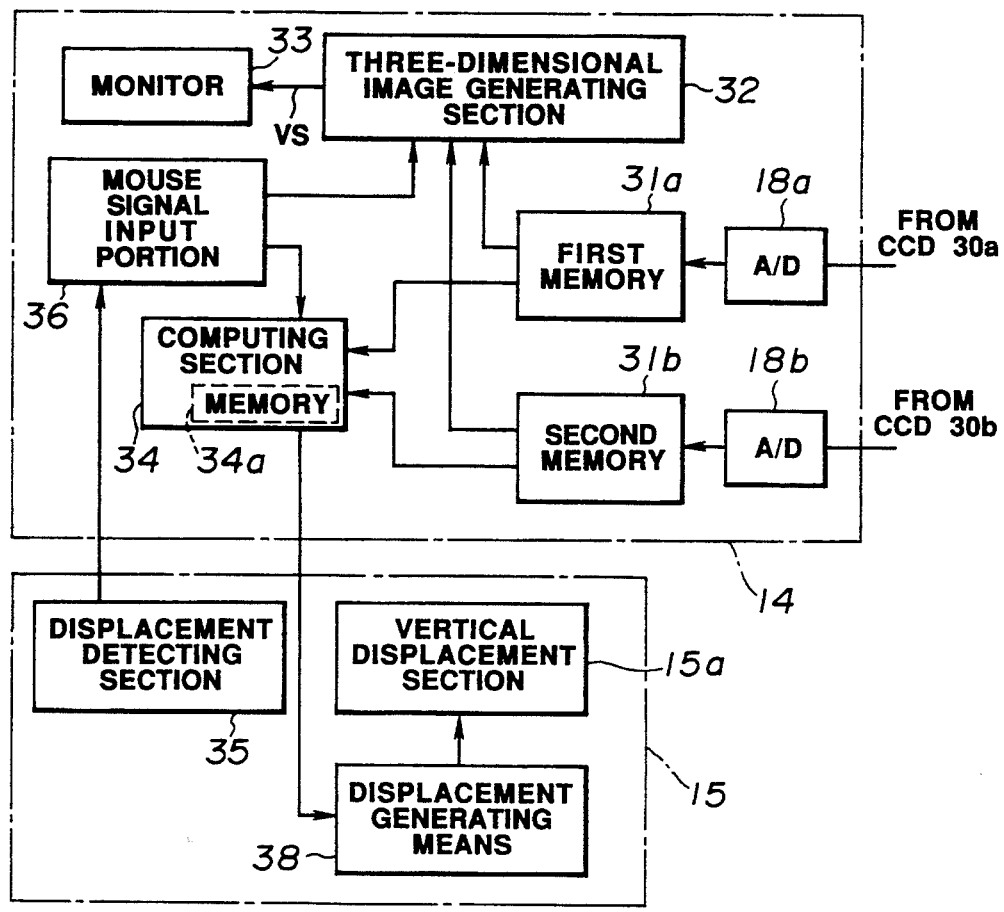
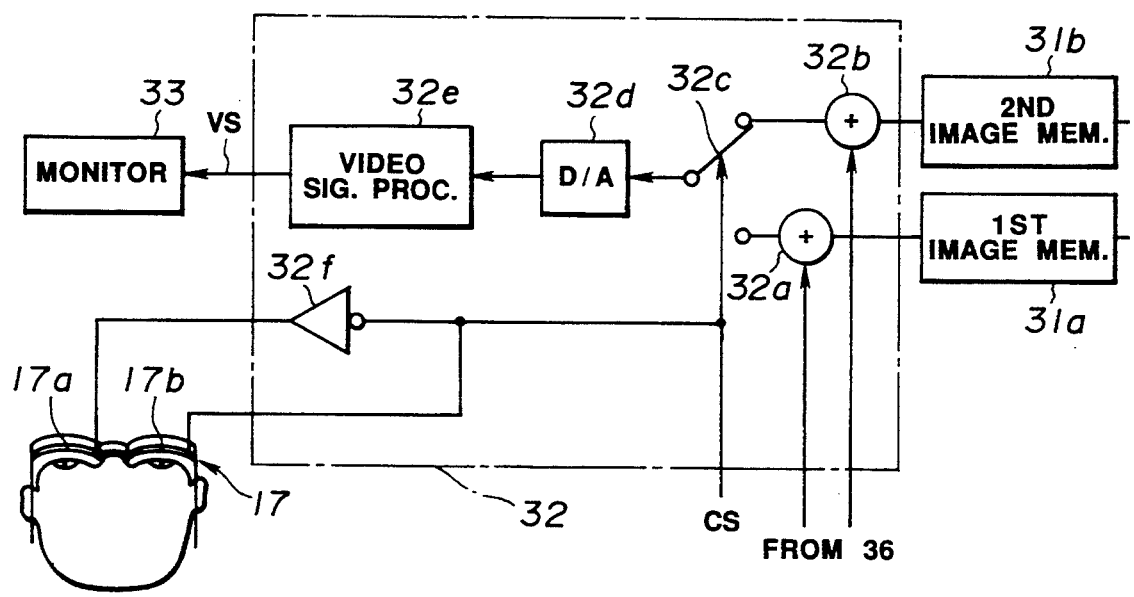

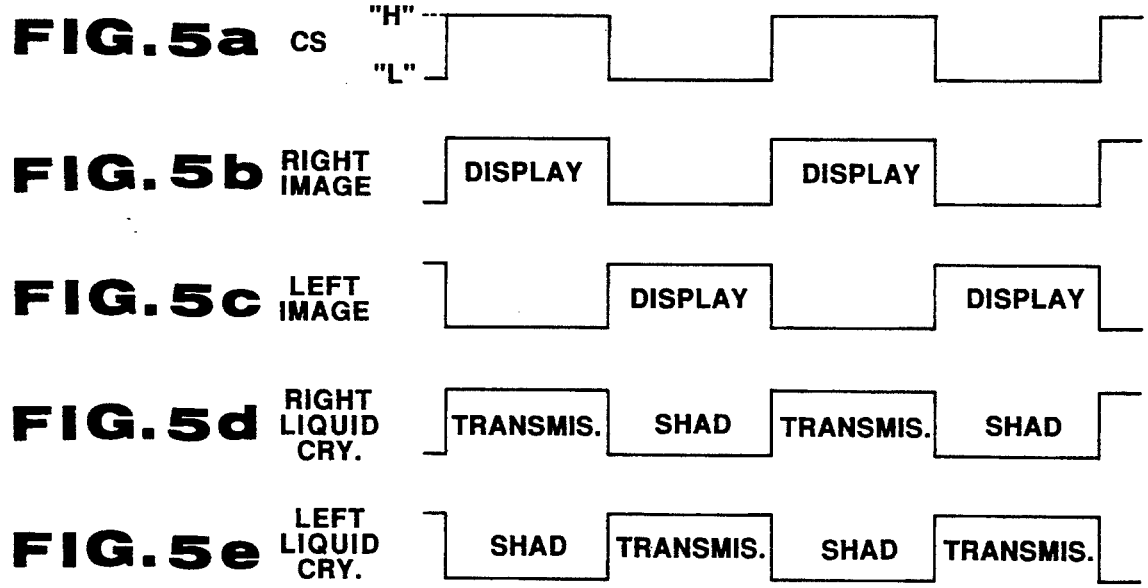
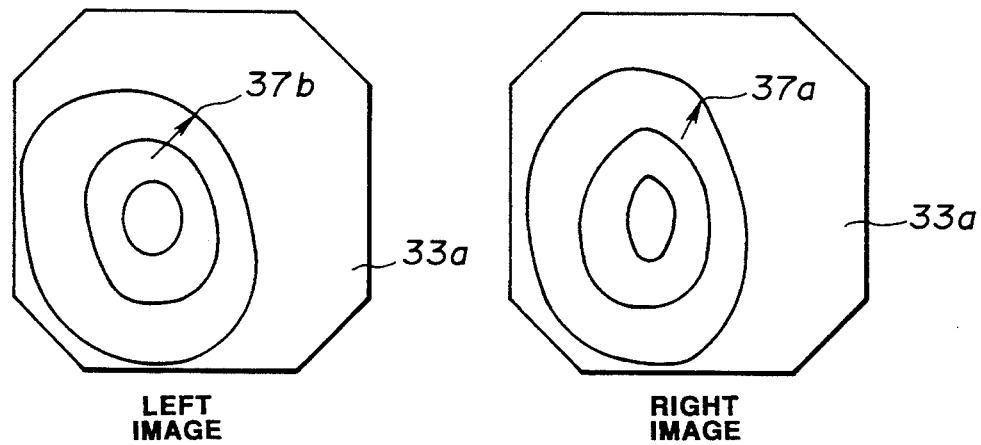

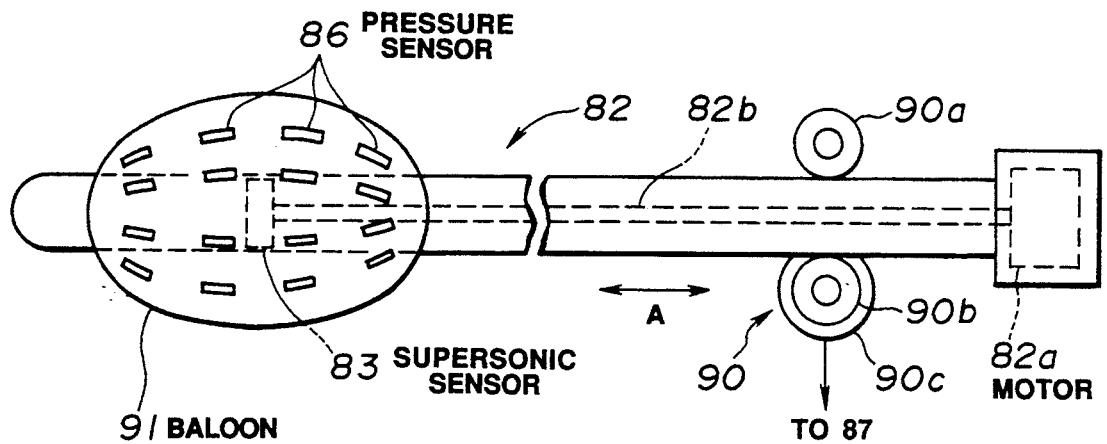
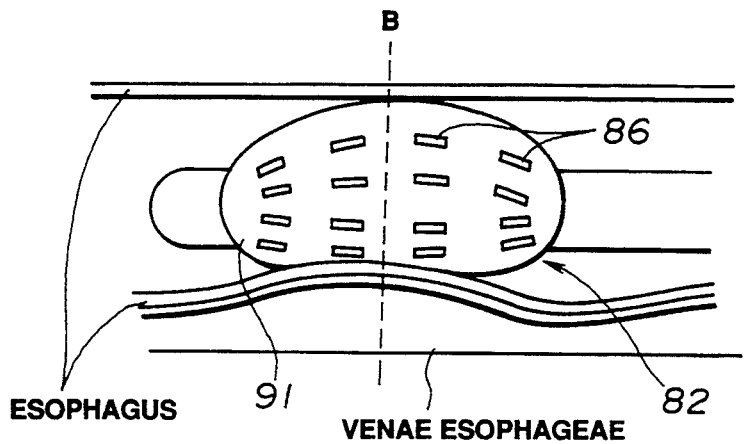
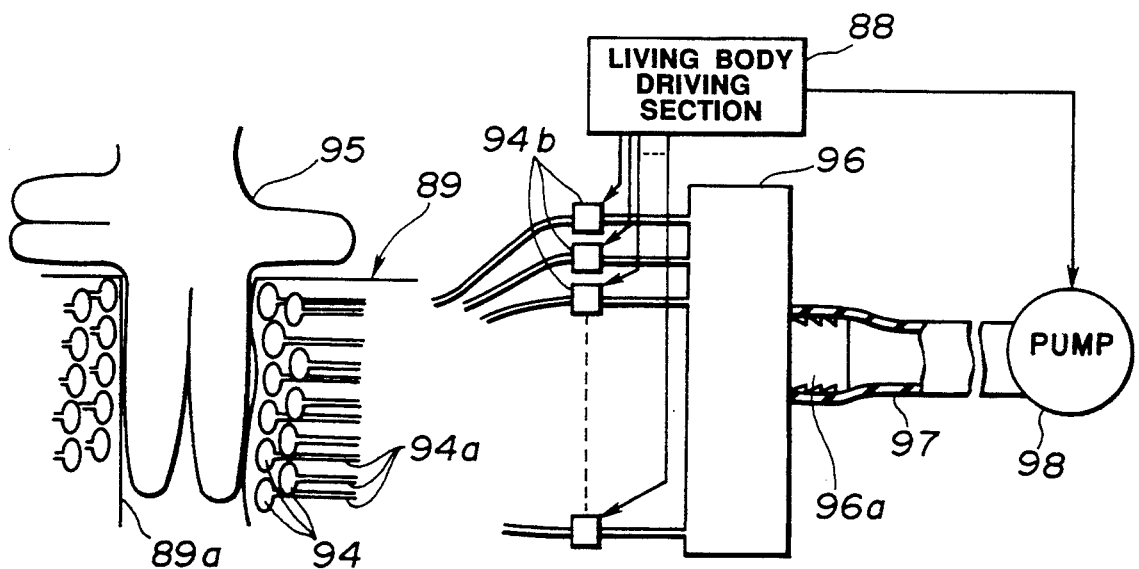

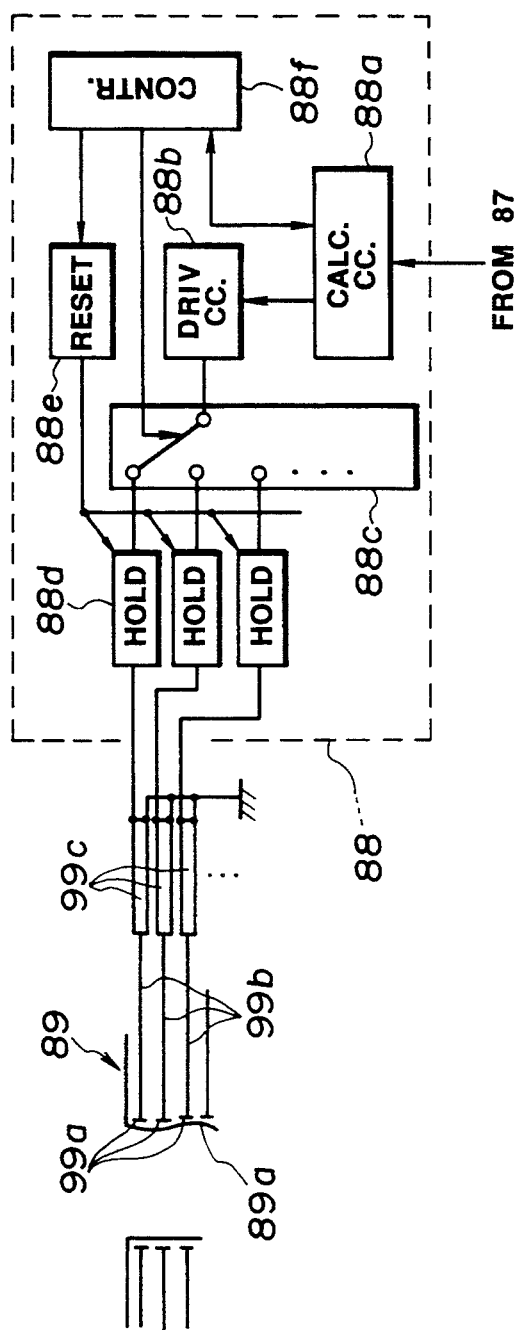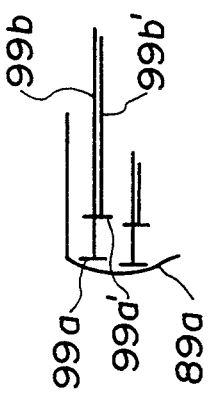

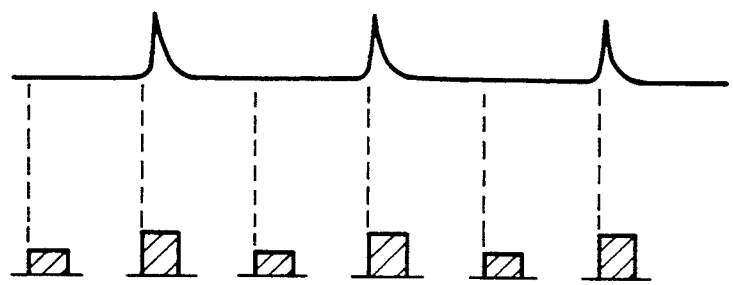
FIG.23a
FIG.23b
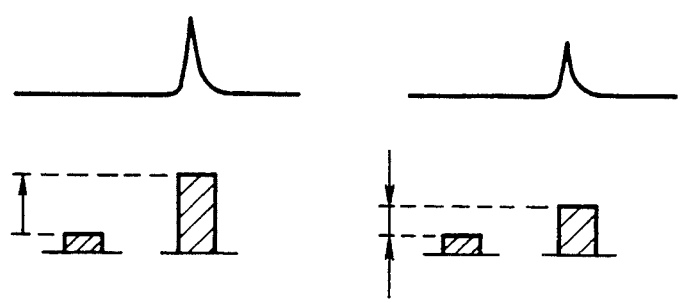
FIG.24a    FIG.24b
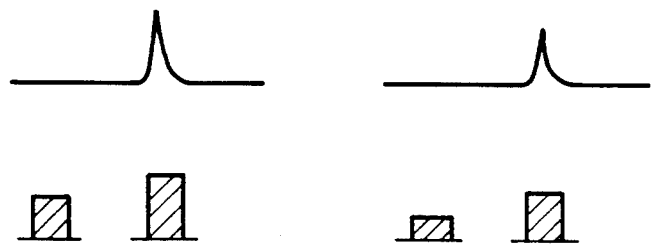
FIG.25a    FIG.25b

MEDICAL SYSTEM HAVING OBJECT INFORMATION REPRODUCTION MEANS FOR PALPATION

BACKGROUND OF THE INVENTION

1. Field of the Invention

The present invention relates to a medical system having an object information reproduction means which is able to reproduce information about the unevenness and the like of a diseased part of a patient, so that a doctor is able to diagnose the diseased part of the object similarly to a case in which the diseased part is directly touched.

2. Description of the Related Art

An endoscope capable of observing a part of an object such as a diseased part in the colon which cannot be directly observed and, if necessary, capable of curing the diseased part by using a curing device has been widely used in a medical field.

For example, if the diseased part of an object is diagnosed in an observation by using an endoscope, it is important for a doctor to know the degree of swelling. Since an image having a parallax cannot be obtained with an ordinary endoscope, it is difficult to visually confirm the unevenness of a diseased part. For example, in Japanese Patent Laid-Open No. 2-216403, there is disclosed an apparatus having a three-dimensional endoscope which includes two object optical systems in order to enable the operator to three-dimensionally observe an object.

Although the shape can be three-dimensionally confirmed with the aforesaid three-dimensional endoscope, an operator (a doctor) cannot confirm in a tactile manner the object. Therefore, information cannot be effectively utilized. For example, a problem arises in that, if there is unevenness the diseased part of an object, the degree of the unevenness of the diseased part cannot be confirmed in a tactile manner.

The aforesaid problem also arises in medical devices except for the endoscopes.

Furthermore, Japanese Patent Laid-Open No. 61-92650 has disclosed a technology which has a detection means for detecting a load current to be applied to a motor for electrically driving a warp-enabled section formed in an endoscope. As a result, an increase in the load current which takes place when the leading portion of an insertion section of the endoscope comes in contact with the inner wall of the colon can be detected. If the aforesaid increase exceeds a predetermined level, an LED is caused to emit light in the visual field of the ocular section via a comparator so as to cause an operator to visually confirm that the subject warping operation is in a dangerous state.

Furthermore, Japanese Patent Laid-Open No. 61-87530 has disclosed a structure having a motor for electrically driving a warp-enabled section formed in an endoscope, a pressure sensor located adjacent to the leading portion of the insertion section and a brake mechanism constituted so as to brake an operation of a warp operating member for warping the warp-enabled section if the pressure detected by the pressure sensor has exceeded a predetermined level. As a result, if the leading portion of the insertion section comes in contact with the inner wall, it is detected by the pressure sensor. If the warp-enabled section is further warped in a direction in which it comes in contact with the inner wall, the operation of the warp operating section for performing the displacing operation is safely inhibited.

Since the aforesaid two publications have been constituted in order to prevent a dangerous warping operation, they cannot improve the diagnosing function of an operator.

Furthermore, Japanese Patent Utility Model Publication No. 2-33761 (Japanese Patent Laid-Open No. 61-65903) has disclosed a structure having a motor which is, via a transmitting shaft, connected to a warp operating member for driving a warp-enabled section formed in an endoscope. The structure further includes a strain gauge connected to the motor for detecting the quantity of the strain of the driving force for warping the member, the driving force being transmitted by the transmitting shaft. If the quantity of the strain detected by the strain gauge is determined to be an abnormal level, a piezoelectric element fastened to the lever for performing the warping operation is driven by an alarm device driving circuit so as to give vibrations to the operator.

In addition, the aforesaid disclosure is arranged in such a manner that the alarm device driving circuit is operated in response to a signal transmitted from a detecting device for detecting the output from the strain gauge whenever a determination has been made that there is a risk that the warp-enabled section of the insertion section is further warped. If a large output from the strain gauge has been detected, the piezoelectric element is vibrated more strongly so as to notify the greater danger.

In general, a doctor intends to synthetically make a diagnosis by maximally utilizing the sense in a tactile manner with the hand in a case where the diseased part can be directly touched by the hand. That is, a doctor makes a diagnosis by utilizing information in a tactile manner (the degree of unevenness, the hardness and/or the fever of the diseased part) obtained in a case where the doctor touches the diseased part by the hand.

However, the conventional technologies have not disclosed a medical system or a medical apparatus with which a diagnosis can be made by utilizing information obtained by palpation if a diseased part which cannot be directly touched by the hand is diagnosed. Therefore, there is a need for a medical system or a medical apparatus with which a further accurate diagnosis can be made.

SUMMARY OF THE INVENTION

An object of the present invention is to provide a medical system which enables an operator to visually diagnose the state of a diseased part and also enables a tactile diagnosing function to be realized in a simulated manner in order to improve the synthetic diagnosing function.

Another object of the present invention is to provide a medical system which enables a diseased part, which cannot be directly diagnosed in a tactile manner, to be diagnosed in a tactile or simulated manner and with which the diagnosing function can be synthetically improved.

As conceptually shown in FIG. 1, a medical system 1 according to the present invention is constituted by detection means 2 for detecting information about a living body or the inside portion of a machine, signal processing means 3 for processing a signal transmitted from the detection means 2 and object information reproduction means 4 which acts according to the output from the signal processing means 3 and which reproduces information about the object. As a result, an operator is able to efficiently confirm information about the living body or the machine by confirming in a tactile manner information by means of the aforesaid object information reproduction means 4.

Other and further objects, features and advantages of the invention will appear more fully from the following description.

BRIEF DESCRIPTION OF THE DRAWINGS

FIGS. 1 to 9 illustrate a first embodiment of the present invention, where

FIG. 1 is a block diagram which illustrates a conceptual structure of the present invention;

FIG. 2 is an overall structural view which illustrates the first embodiment of the present invention;

FIG. 3 is a block diagram which illustrates the structure of an essential portion according to the first embodiment;

FIG. 4 is a block diagram which illustrates the structure of a three-dimensional image generating section;

FIGS. 5a–e illustrate a state in which a three-dimensional observation can be realized;

FIG. 6 illustrates a state in which the position of a cursor which corresponds to the position of a cursor on a right image displayed on a monitor is set on a left image;

FIG. 7 illustrates a principle of obtaining the quantity of unevenness;

FIG. 8 is a cross-sectional view which illustrates a state in which a vertical displacement section, which vertically displaces according to the quantity of the unevenness, is formed in a mouse;

FIG. 9 is a circuit diagram which illustrates the structure of a displacement generating means;

FIGS. 10 to 14 illustrate a second embodiment of the present invention, where

FIG. 10 is a block diagram which illustrates the overall structure of the second embodiment;

FIG. 11 is a side elevational view which illustrates a probe according to the second embodiment;

FIG. 12 illustrates a state in which the probe shown in FIG. 10 has been inserted into the esophagus;

FIG. 13 illustrates an example of a living model according to the second embodiment;

FIGS. 14a and 14b illustrate another example of the living model according to the second embodiment;

FIG. 15 illustrates the overall structure of the third embodiment;

FIG. 16 is a cross-sectional view which illustrates a mouse according to the third embodiment;

FIG. 17 is a block diagram which illustrates the structure of a main control unit according to the third embodiment;

FIG. 18 illustrates the overall structure of the fourth embodiment;

FIG. 19 is a cross-sectional view which illustrates a leading portion of a supersonic endoscope according to the fourth embodiment;

FIG. 20 is a side elevational view which illustrates an essential portion according to a modification to the fourth embodiment;

FIGS. 21 to 26 illustrate a fifth embodiment of the present invention, where

FIG. 21 is a structural view which illustrates a state in which the system according to the fifth embodiment is being used;

FIG. 22 is a structural view which illustrates a living body information detecting section and the like according to the fifth embodiment;

FIGS. 23a and 23b illustrate a method of driving a stimulus generating element in response to heartbeats;

FIGS. 24a and 24b illustrate a method of driving a stimulus generating element in response to the blood pressure;

FIGS. 25a and 25b illustrate a method of driving a stimulus generating element in response to the concentration of oxygen; and FIG. 26 is a block diagram which illustrates the specific structure of a living body information signal processing circuit and the like according to the fifth embodiment.

DETAILED DESCRIPTION OF THE PREFERRED EMBODIMENTS

Figure 7:
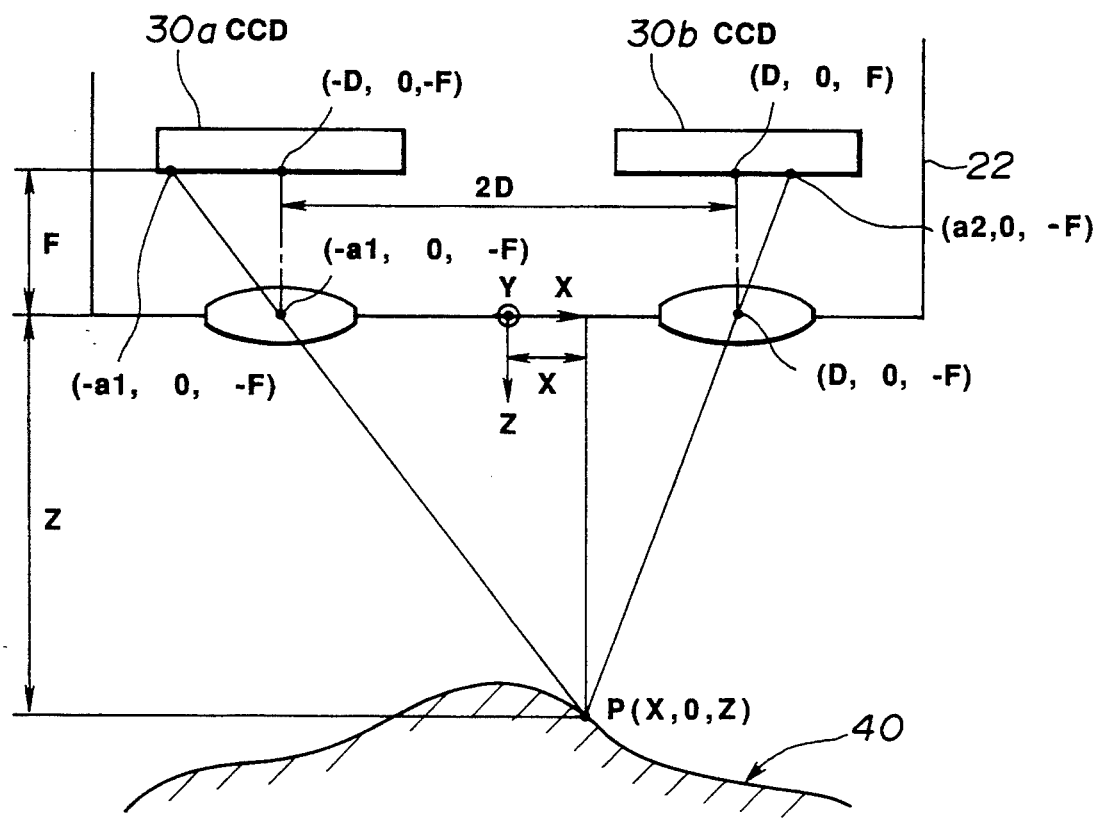

As shown in FIG. 2, an endoscope system 1 serving as a medical system according to a first embodiment of the present invention comprises a three-dimensional electronic scope 12 for obtaining a three-dimensional image, a light source device 13 for supplying illuminating light-rays to the electronic scope 12, an information processing device and monitor 14 for processing a signal obtained by an image pickup means of the electronic scope 12 and displaying an image on a monitor scope 33a, and a mouse 15 having a vertical displacement section 15a (which serves as an unevenness quantity reproduction means) which is vertically displaced according to the quantity of the unevenness of an instructed position of the imaged object in response to a signal transmitted from the information processing device and monitor 14.

The aforesaid three-dimensional electronic scope 12 has an elongated insertion section 16, a wide operating section 18 formed at the rear end portion of the insertion section 16 and a universal cable 19 extending from the operating section 18. By connecting a connector 20 disposed at the leading portion of the universal cable 19 to the light source device 13, white illuminating light-rays emitted from a lamp 13a of the light source device 13 are concentrated by a lens 13b so as to be supplied to an incident end surface 28a of a light guide 28.

Furthermore, a signal cable 21 is extended from the aforesaid connector 20 via a signal connector 21a in such a manner that the signal cable 21 can be connected to the information processing device and monitor 14.

The aforesaid insertion section 16 has a solid leading section 22, a warp-enabled section 23 which can be warped and a flexible section 24 which can be flexed which are respectively formed in this order when viewed from the leading portion. The operating section 18 has an angle operation knob 25 with which either of a pair of wires 29 can be pulled and another wire 29 is slackened so as to vertically/horizontally warp the warp-enabled section 23.

The illuminating light-rays supplied from the light source device 13 are transmitted through the light guide 28, and are, via an illuminating lens 26, further forwardly emitted from an end surface secured to the leading section 22, so that an object 40 is irradiated with the illuminating light-rays. The optical image of the object 40 thus irradiated with the illuminating light-rays is formed on each of CCDs 30a and 30b disposed on the focal planes, the optical images being formed by objective lenses 27a and 27b disposed away from each other in the leading section 22. The optical images are photo-electrically converted by the CCDs 30a and 30b, so that image signals are generated and are supplied to the information processing device and monitor 14 shown in FIG. 3 via a signal line 19.

The image signals supplied to the aforesaid information processing device and monitor 14 are converted by A/D converters 18a and 18b so as to be digital image data items. The digital image data items are then supplied to first and second image memories 31a and 31b for storage. The image data stored in each of the image memories 31a and 31b is read out and supplied to a three-dimensional image generating section 32. In the three-dimensional image generating section 32, the image data is subjected to a signal processing operation and confirmed as a three-dimensional image. As a result, a standard video signal VS is generated and is displayed on a monitor 33, so that it is visually confirmed by an operator as a three-dimensional image.

The two image data items memorized in first and second image memories 31a and 31b are also supplied to a computing section 34, so that the quantity of the unevenness of the image is computed by using the aforesaid image data.

On the other hand, the two-dimensional displacement of the mouse 15 is detected by a displacement detecting section 35 composed of a rotatable ball 15c and a rotary encoder section 15d (see FIG. 8), and a signal denoting the result of the detection is transmitted to a mouse signal input portion 36.

The mouse signal input portion 36 computes the position (the present position) of the mouse 15 after it has been displaced by the rotational displacement of the ball 15c from the initial position of the mouse 15. The mouse signal input portion 36 transmits a cursor character to the three-dimensional generating section 32. Therefore, a cursor 37a is displayed on the scope 33a of the monitor 33 at a position dictated by the position of the mouse 15 (see FIGS. 2 and 6).

The three-dimensional image generating section 32 for processing the signal in order to display it so that it is confirmed as the three-dimensional image is, for example, structured as shown in FIG. 4.

Right and left image data items memorized in the first and the second image memories 31a and 31b are respectively supplied to contacts a and b of a switch 32c via corresponding mixers 32a and 32b. The switch 32c is alternately switched in response to switch signal CS. A signal selected by the switch 32c is then converted into an analog signal by a D/A converter 32d, the analog signal being then converted into a standard video signal such as an NTSC system by a video signal generating circuit 32e. Then, the video signal is transmitted to the monitor 33, so that right and left images are alternately displayed on the monitor scope 33a at a predetermined cycle as shown in FIG. 6.

The cursor character transmitted from the mouse signal input portion 36 is, together with, for example, the image data memorized in the first image memory 31a, supplied to the switch 32c via the mixer 32a. As a result, the cursor character is displayed on the right image as shown in FIG. 6, the cursor character being formed into, for example, an arrow shape when it is displayed.

In order to display a cursor 37b for determining the position on the left image data which corresponds to the position of the cursor 37a on the right image data memorized in the first image memory 31a, the mouse signal input portion 36 supplies the cursor character to the switch 32c via the mixer 32b together with the image data memorized in the second image memory 31b.

The switch signal CS for switching the switch 32c is supplied to a right liquid crystal 17a of liquid crystal glasses 17, and is also supplied to the left liquid crystal 17b via an inverter 32f. As a result, the right glass section and the left glass section of the liquid crystal glasses 17 are alternately switched between the light transmissible state and the light shielded state.

That is, the right liquid crystal 17a and the left liquid crystal 17b of the liquid crystal glasses 17 are alternately switched between the transmissible state and the light shielded state in synchronization with the alternate display of the right image and the left image made on the monitor 33. As a result, an operator with the aforesaid liquid crystal glasses 17 is able to see a three-dimensional image. FIG. 5 illustrates images displayed in synchronization with the switch signal CS and also illustrates the light transmissible state and the light shielded state of the liquid crystal glasses 17.

The switch signal CS shown in FIG. 5A is a pulse having a duty of 50%. When the level of the pulse is "H", the right image data memorized in the first image memory 31a is selected. As a result, the right image is displayed on the monitor 33 as shown in FIG. 5B. When the level of the aforesaid pulse is "L", the left image data memorized in the second image memory 31b is selected. As a result, the left image is displayed on the monitor 33 as shown in FIG. 5C. If the aforesaid pulse is "H", the right liquid crystal 17a of the liquid crystal glasses 17 is brought to a light transmissible state as shown in FIG. 5D. As a result, the right image can be confirmed by the right eye of the operator. At this time, the left liquid crystal 17b is brought into a light shielded state. On the other hand, if the aforesaid pulse is "L", the left liquid crystal 17b of the liquid crystal glasses 17 is brought into a light transmissible state as shown in FIG. 5E. As a result, the left image can be confirmed by the left eye of the operator. At this time, the right liquid crystal 17a is brought into the light shielded state. Therefore, the operator is able to three-dimensionally confirm the state of the object from the two images.

In the method of detecting the unevenness, the display of the displaced position of the mouse 15 is made on either image (on the right image according to this embodiment) and the display of the cursor 37a which corresponds to the aforesaid position is made on only the right image. The position on the left image which corresponds to the position of the cursor 37a is set by the operator. In a case where the cursor 37a on the right image is instructed as shown in FIG. 6, the cursor 37b for instructing the corresponding position on the left image is also displayed on the left image. Furthermore, the operator displaces the position to the corresponding position by the ball 15c of the mouse 15 and depresses a click button 15b at this position, so that the position of the cursor which corresponds to the position of the cursor 37a is determined.

Information about the position of the cursor 37b which corresponds to information about the position of the cursor 37a is memorized by, for example, a position information recording memory 34a of the computing section 34. The position on the left image which corresponds to the position on the right image is read out from the position information recording memory 34a when a calculation for obtaining the quantity of unevenness at the position on the right image instructed by the cursor 37a is performed. The position on the left image thus read out is used to perform the calculation.

Signals corresponding to the positions of the two cursors 37a and 37b are transmitted from the mouse 15 to the computing section 34. The computing section 34 obtains the quantity of unevenness at the position on the surface of the endoscope image displayed on the monitor 33 from data about the position on the right image instructed by the mouse 15 and data about the corresponding position on the left image read from the memory 4a. The computing section transmits the quantity of the unevenness to a displacement generating means 38.

The displacement generating means 38 vertically displaces a vertical displacement section 15a according to the output from the computing section 34, so that the unevenness of a portion of the object imaged by the endoscope and instructed by the cursor 37a is reproduced by means of the vertical displacement.

FIG. 7 illustrates the principle of an operation of measuring the quantity of the unevenness performed by the computing section 34. The distance 2D between the two objective lenses 27a and 27b and the focal distance F of each of the objective lenses 27a and 27b are known values. In order to simplify the description, the calculation of the quantity of the unevenness of the position P of the surface of the object 40 at Y coordinates=0 will now be described (the quantity of the unevenness at the Y coordinates=0 is calculated, that is, value Z of Z coordinates of the position P of the object 40 is calculated in this case).

The position P of the object 40, the coordinates of which are (X, O, Z), is imaged on coordinates $(-a1-D, O\ -F)$ and $(a2+D, O, -F)$ on the image pick-up surface of the CCDs 30a and 30b by the objective lenses 27a and 27b. By using the relationship for the similarity of triangles, the following relationships are held:

$$a1-D{:}F=D+X{:}Z \quad (1)$$

$$a2-D{:}F=D-X{:}Z \quad (2)$$

From the aforesaid two equations, the Z coordinates which correspond to the quantity of the unevenness of the position P on the surface of the object 40 can be obtained by the following equation:

$$Z=2D(F+1)/(a1+a2) \quad (3)$$

In Equation (3), a1 is determined by the position of the cursor 37a, while a2 is read out from the memory 34a. Since the structure shown in FIG. 7 is arranged in such a manner that the Z coordinates are set in a direction in which the value of Z is increased, a fact that the position P projects is shown if the position P, the value Z of which is slightly increased from value Z0, is present.

Figure 8:
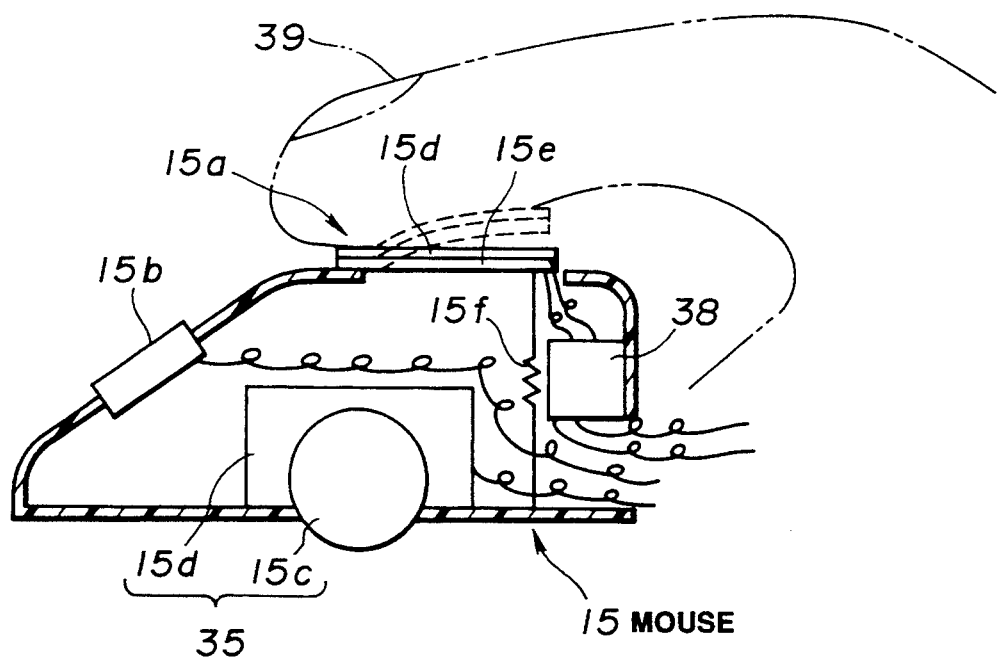

FIG. 8 illustrates the structure of the vertical displacement section 15a of the mouse 15. The mouse 15 has the click button 15b, the ball 15c and the encoder section 15d for detecting the quantity of the displacement from the amount of rotation of the ball 15c. Furthermore, the mouse 15 has the vertical displacement section 15a which is vertically displaced. The vertical displacement section 15a is formed by, for example, two band-like (plate-like) piezoelectric elements 15d and 15e. The piezoelectric elements 15d and 15e are respectively expanded/contracted in the lengthwise direction according to a value of a D.C. current supplied to electrodes fastened to their two sides. If the absolute values of the levels of the voltage applied to the electrodes are large, the quantity of the expansion/contraction becomes large. The expansion/contraction is made according to the polarity of each of the electrodes.

An end portion of either of the aforesaid piezoelectric elements 15d and 15e is secured to the outer frame for the mouse 15, while another end portion of the same is urged downwards by a spring 15f. Furthermore, the piezoelectric elements 15d and 15e are arranged to receive DC driving signals supplied from the displacement generating means 38. For example, when a DC voltage, the level of which is in proportion to a quantity Z0−Z obtained by subtracting the aforesaid Z from a certain reference value Z0, is generated by the displacement generating means 38 and is applied to each of the piezoelectric elements 15d and 15e in such a manner that the piezoelectric elements 15d and 15e respectively receive DC voltages of inverse polarities, for example, the upper piezoelectric element 15d is deformed (in a case where Z0−Z>0) in such a manner that it expands, causing the lower piezoelectric element 15e to be deformed in such a manner that it contracts.

Therefore, when the position is shifted to, for example, a portion which projects over a certain value Z0 (when the position is shifted, for example, to the left from the position shown in FIG. 7), the two piezoelectric elements 15d and 15e are deformed as designated by a dashed line shown in FIG. 8. As a result, by placing a hand 39 on the vertical displacement section 15a constituted by the piezoelectric elements 15d and 15e, the degree of the unevenness of the surface of the object 40 can be confirmed in a tactile manner according to the vertical displacement of the vertical displacement section 15a.

Figure 9:
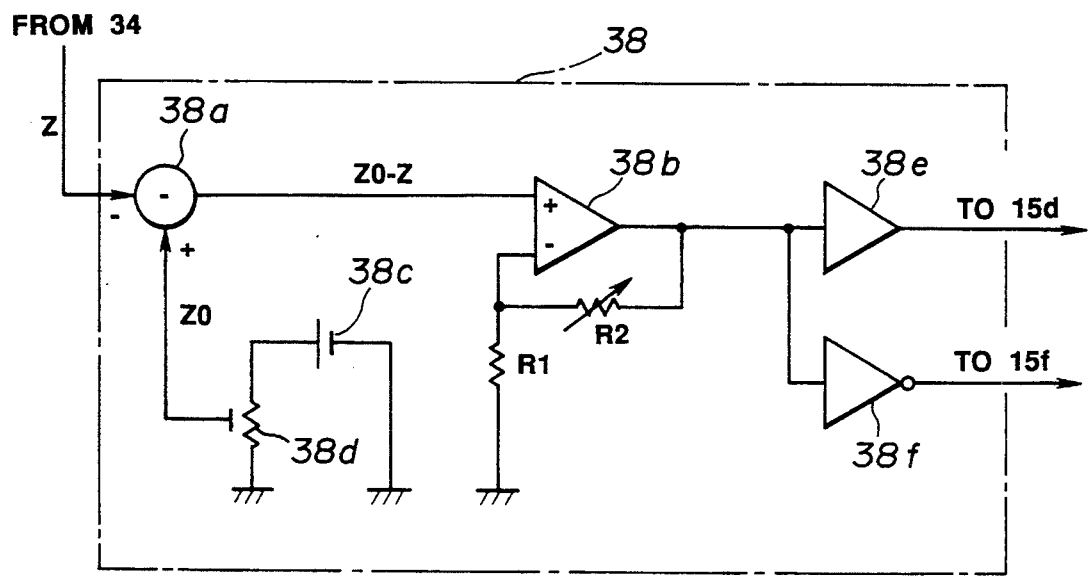

FIG. 9 illustrates the structure of the displacement generating means 38. Signal Z supplied from the computing section 34 is supplied to an operational amplifier (hereinafter called an "OP-AMP") 38b via a subtracter 38a. Furthermore, the reference value Z0 obtained by dividing constant voltage V of a power source 38c by a variable resistance 38d is applied to the subtracter 38a. The subtracter 38a transmits a signal denoting the value of the subtraction Z0−Z to the OP-AMP 38b. The OP-AMP 38b amplifies the signal with a gain (1+R2/R1) determined by resistors R1 and R2. Then, the amplified signal is made to be a driving signal via buffers 38e and 38f so as to be supplied to the piezoelectric elements 15d and 15e of the vertical displacement section 15a.

The resistance R2 is a variable resistance having a dial for use to vary the gain when it is operated by the operator. Therefore, the quantity of the unevenness obtained due to computing performed by the computing section 34 can be reproduced while being enlarged by the vertical displacement section 15. That is, a means is constituted which is able to set the vertical displacement made by a degree which corresponds to the unevenness obtained by the computing section 34 to an arbitrary multiple of the unevenness computed by the computing section 34.

Furthermore, the reference value Z0 to be set can be varied by the variable resistance 38d.

According to the first embodiment, when the operator puts the forefinger or the like of the hand 39 on the vertical displacement section 15a of the mouse 15 as shown in FIG. 8 and displaces the cursor 37 to a desired position of the endoscope image, the quantity of the unevenness of the position pointed to by the cursor is computed by the computing section 34. As a result, the vertical displacement section 15a of the mouse 15 is vertically displaced by a quantity corresponding to the quantity of the unevenness obtained by the calculation.

Therefore, when the operator displaces the mouse 15 on the endoscope image, the quantity of the unevenness of the range in the endoscope image in which the mouse 15 has been displaced is transmitted to the finger (the hand) with the vertical displacement of the vertical displacement section 15a. As a result, the surface of the object 40 can be confirmed in a tactile manner.

On the other hand, the operator is able to recognize in a tactile manner the object 40 as well as able to three-dimensionally recognize the object 40 from the image on the monitor 33. Therefore, the operator is able to further exactly make a diagnosis.

The vertical displacement section 15a may be made of a shape-memory alloy or formed into a structure which is vertically displaced by air pressure. It is not limited to the vertical displacement structure. Therefore, a structure which is displaced (driven) horizontally may be employed. Although the first embodiment is arranged in such a manner that the quantity of the unevenness is reproduced by the one-dimensional displacement operation, the quantity of the unevenness may be reproducing along a line, or the same may be reproduced in a two-dimensional range. For example, by utilizing a living model 89 and a driving mechanism for driving it to be described later with reference to FIG. 14A, the quantity of the unevenness can be reproduced in a two-dimensional range.

Although the first embodiment is arranged in such a manner that the two images obtained by the two optical image pick-up means are displayed in the time-shared manner so as to be three-dimensionally confirmed by the operator, another structure may be employed in which a three-dimensional signal denoting a three-dimensional image is generated in the three-dimensional image generating section 32 and this three-dimensional image is displayed on the monitor 33.

Figure 10:
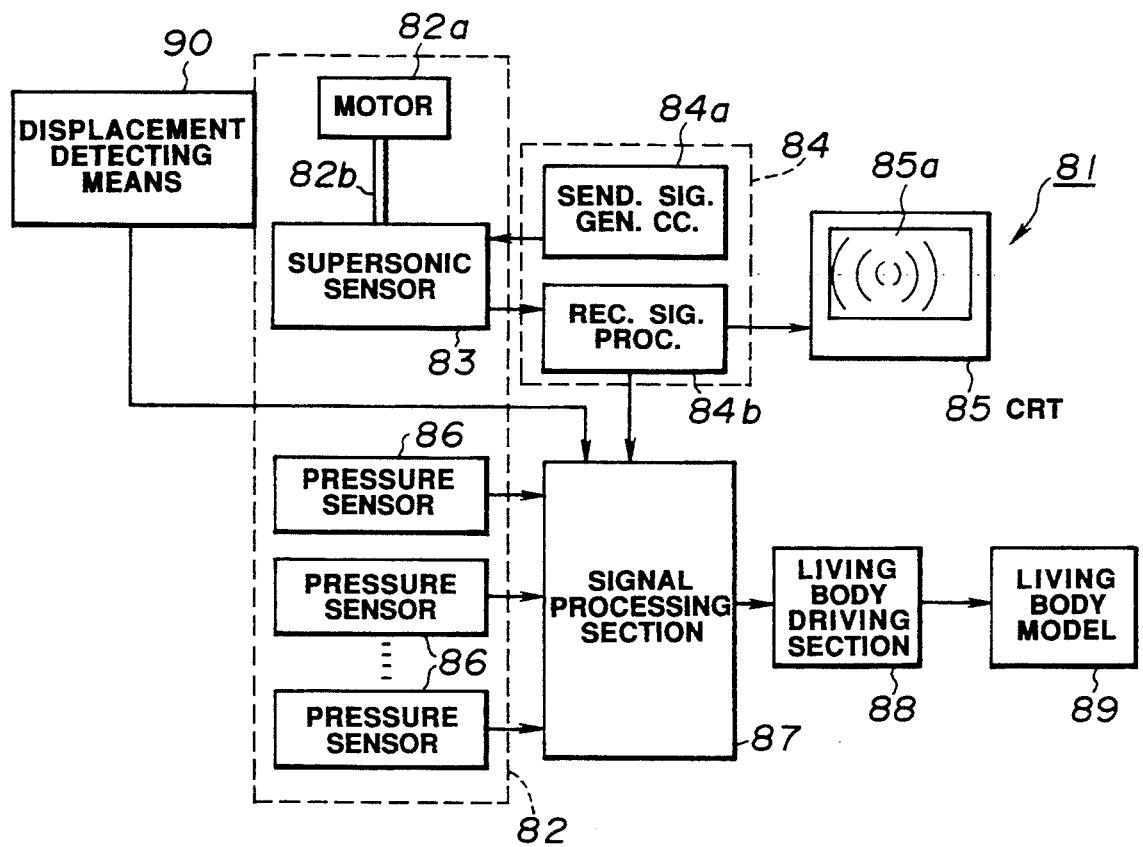

FIG. 10 illustrates a living-body palpation device 81 according to a second embodiment of the present invention. The living-body palpation device 81 has an elongated probe 82 to be inserted into, for example, the esophagus, the probe 82 having a supersonic sensor 83 rotatively accommodated at the front end portion thereof.

The supersonic sensor 83 receives a transmission pulse transmitted from a transmission signal generating circuit 84a located in a supersonic signal processing section 84 to transmit a supersonic wave. Furthermore, the supersonic sensor 83 receives the wave reflected by a portion of the object at which the acoustic impedance is changed so as to convert it into an electric signal. The supersonic sensor 83 is, in the probe 82, rotated by a motor 82a via a flexible shaft 82b, the supersonic sensor 83 radially transmitting/receiving the supersonic wave when it is rotated.

The signal received by the supersonic sensor 83 is processed by a received-signal processing circuit 84b disposed in the supersonic signal processing section 84. Then, a supersonic tomographic image 85a is displayed on a CRT 85. The supersonic tomographic image is displayed after the level of the reflected wave has been brightness-modulated according to the distance from the supersonic sensor 83.

The aforesaid probe 82 has an ovoid balloon 91 at the leading portion thereof as shown in FIG. 11, the balloon 91 having a configuration of a multiplicity of pressure sensors 86 fastened to the surface thereof. A pressure signal detected by each pressure sensor 86 is supplied to a signal processing section 87. Furthermore, the probe 82 has, on the base portion thereof, a displacement detection device 90 for detecting the displacement of the probe 82 in a longitudinal direction A. The displacement detection device 90 comprises rollers 90a and 90b positioned in contact with the surface of the probe 82 so as to be rotated. The displacement detection device 90 further comprises a rotary encoder 90c fastened to the rotational shaft of the roller 90b.

The signal processing section 87 receives the pressure signal supplied from the pressure sensor 86, the supersonic signal supplied from the supersonic signal processing section 84 and an output corresponding to the displacement and supplied from the rotary encoder 90c. The supersonic signal is used to obtain the shape of the observed portion, the pressure signal is used to obtain the hardness of the observed portion and the output signal from the rotary encoder 90c is used to obtain the displacement. Information thus obtained is transmitted to a living model driving section 88. The living model driving section 88 three-dimensionally deforms the living model 89 so as to be the same shape as the observed portion according to supplied information.

The balloon 91 disposed at the leading portion of the probe 82 shown in FIG. 11 is inflated with water which is capable of propagating the supersonic wave (because, if it is inflated with air, the propagation of the supersonic is substantially prevented).

FIG. 12 illustrates a state where the probe 82 has been inserted so as to diagnose venae esophageae carcinoma. The tomographic image of the plane designed by a dashed line B is imaged by means of the supersonic wave. Since the pressure sensors 86 are fastened in such a manner that they do not overlap the tomographic image, the images of the pressure sensors 86 are not formed in the supersonic image.

FIG. 13 illustrates an example of the living model 89. The living model 89 is, for example, constituted in such a manner that a multiplicity of small balloons 94 are disposed adjacent to the wall surface of a cylindrical hollow section 89 formed in an elastic member. When the balloons 94 disposed adjacent to the wall surface of the hollow section 89 are expanded/contracted, the living model 89 is deformed so as to become the same shape as that of the observed portion. By touching the living model 89 by a hand 95, the size and the hardness of the diseased part can be confirmed.

Each balloon 94 is connected to a hollow container 96 via a guide tube 94a and an electromagnetic valve 94b. The hollow container 96 has a joint 96a to which an end portion of the tube 97 is connected. Another end portion of the tube 97 connected to the joint 96a is connected to a pump 98.

The electromagnetic valve 94b and the pump 98 are controlled by a living body driving section 88. The quantity of air to be supplied to each balloon 94 is determined according to, for example, information supplied from the signal processing section 87. Then, the electromagnetic valve 94b, which is connected to the balloon 94, is set to a predetermined minimum quantity of air, and is opened so that it communicates with the hollow container 96. The living model driving section 88 operates the pump 98 to control the quantity of air to be supplied to the balloon 94 to the predetermined quantity. Then, the aforesaid electromagnetic valve 94b is closed, and the balloon 94 which must be set to the air quantity of a second level is controlled similarly. By repeating the aforesaid control, all of the balloons 94 are set to air quantities which are suitable to reproduce the living body.

This embodiment enables a diagnosis to be made in such a manner that the venae esophageae carcinoma is palpated from the inside portion of the esophagus, the diagnosis of this type being impossible to be made with an actual living body. The living model 89 may be constituted, as shown in FIG. 14A, in such a manner that the end portions of wires 99b, to which pins 99a are fastened to the other end portions, are fastened to piezoelectric elements 99c which are respectively driven by the living model driving section 88. Furthermore, an actuator mechanism is constituted in which each piezoelectric element 99c is expanded/contracted due to the aforesaid driving operation so as to horizontally displace each pin 99a when viewed in FIG. 14A. By deforming the actuator mechanism according to the living body, the unevenness of the living body can be two or three-dimensionally reproduced.

Furthermore, when the displacement of the pin 99a' facing the pin 99a as shown in FIG. 14B is controlled by means of the wire 99b', the hardness of the elastic member facing the hollow section 89a is changed. As a result, the hardness of the living body can be reproduced.

In a case where the aforesaid actuator mechanism is employed, the living model driving section 88 calculates the degree of driving each piezoelectric element 99c according to information supplied from the signal processing section 87, the calculation being performed in a computing circuit 88a of the living model driving section 88. The output from the computing circuit 88a is supplied to a hold circuit 88d composed of a capacitor or the like via a driving circuit 88b and a switch 88c. The hold circuit 88d continues to supply a driving signal transmitted from the driving circuit 88b via the switch 88c to the piezoelectric element 99c until it receives a reset signal transmitted from a reset circuit 88e. The calculations to be performed by the computing circuit 88a, the switching operation to be performed by the switch 88c and the resetting operation to be performed by the reset circuit 88e are controlled by a controller 88f.

When cancer of the rectum is diagnosed, whether or not an indulation is present is examined by directly inserting a finger into the anus of the patient, causing problems in terms of safety and sanitation. However, this embodiment is able to overcome the sanitation problem because of eliminating the necessity of directly touching the diseased part. Furthermore, this embodiment can be used to diagnose a deep part into which the finger cannot be inserted.

Figure 15:
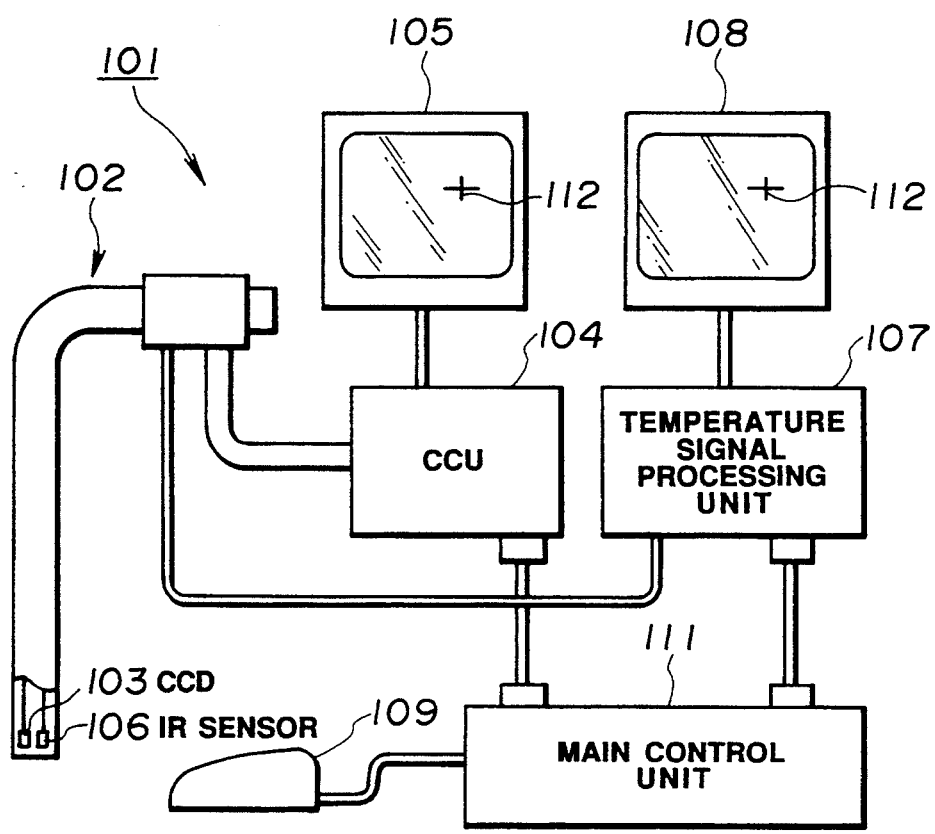
FIGS. 15 to 17 illustrate a third embodiment of the present invention, where

FIG. 15 illustrates a medical system 101 with a temperature sensitive function according to a third embodiment of the present invention. The system 101 is constituted by an electronic scope 102, a camera control unit (hereinafter abbreviated to a "CCU") 104 for processing a signal transmitted from a CCD 103 of the electronic scope 102, an endoscope image display monitor 105 for displaying a video signal processed by the CCU 104, a temperature signal processing unit 107 for processing temperature information detected by an infrared ray sensor 106 provided for the electronic scope 102 so as to obtain a temperature distribution image, a temperature distribution image display monitor 108 for displaying the temperature distribution image from an output signal processed by the temperature signal processing unit 107, a mouse 109 for instructing a marker position and a main control unit 111 for performing processing including a process for reproducing the temperature of a position marked by the marker instructed by the mouse 109 in a temperature reproduction section 110 provided for the mouse 109.

Figure 16:
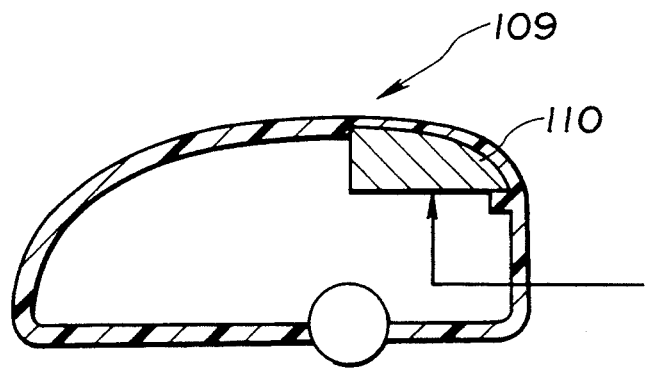

The medical system 101 is arranged in such a manner that the electronic scope 102 is provided with the infrared ray sensor 106 for detecting the temperature of a part to be diagnosed, the detected temperature is processed in the temperature signal processing unit 107 and the temperature distribution image is displayed on the monitor 108. Furthermore, the mouse 109 is used to displace the position of the marker 112 on the endoscope image and the temperature distribution image. The mouse 109 has a temperature reproduction section 110 made of a Peltier device or the like as shown in FIG. 16. The temperature reproduction section 110 is located, for example, at a position on which the forefinger is placed.

Figure 17:
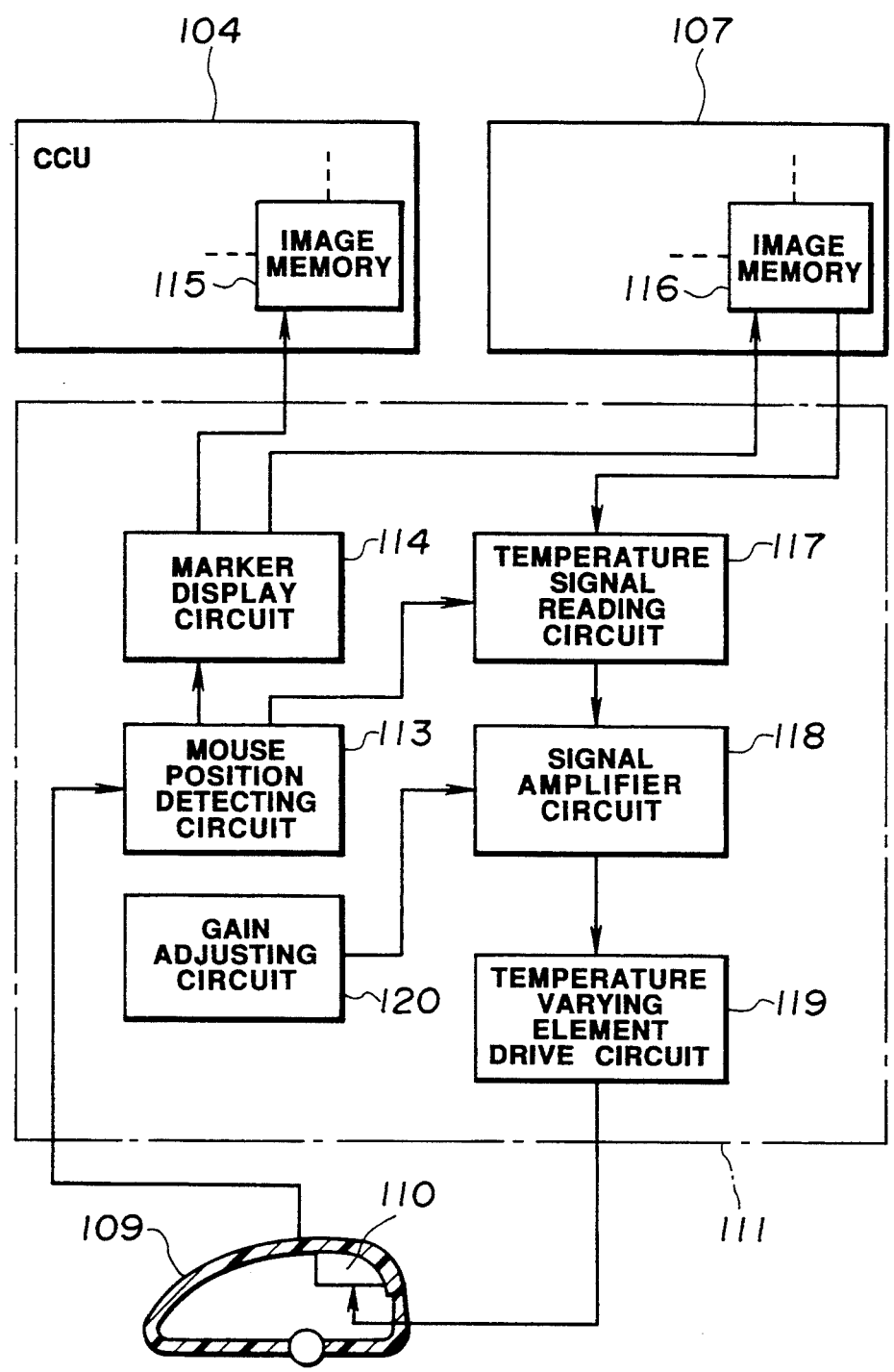

FIG. 17 illustrates a detailed structure of the main control unit 111 of the medical system 101. A signal denoting the position (amount of the displacement) of the mouse 109 is supplied to a mouse position detecting circuit 113, so that the position of the mouse 109 is detected. A signal denoting the detected position is, via the marker display circuit 114, memorized in each image memories 115 and 116 in the CCU 104 and the temperature signal processing unit 107. As a result, the marker 112 is displayed on the monitors 105 and 108.

The image memory 116 disposed in the temperature signal processing unit 107 is connected to a temperature signal reading circuit 117. As a result, the signal denoting the temperature of a portion at which the marker 112 is positioned is read by using a signal of the mouse position detecting circuit 113, the signal being then amplified by a signal amplifying circuit 118. As a result of this amplification, the temperature change is enlarged so as to cause a slight temperature change to be judged by the temperature sensitivity of the hand. Then, the temperature signal is transmitted to a temperature varying element driving circuit 119. The driving circuit 119 drives a temperature varying section 110.

The signal amplifier circuit 118 has an amplification ratio which can be varied by a gain adjustment circuit 120. According to this embodiment, the temperature of the portion suspected to be a diseased part can be confirmed by observing the endoscope image. Therefore, the diagnosis can be made also depending upon the temperature as compared with the conventional structure which depends only the visual information. As a result, the diagnosis can be more accurately made.

Figure 18:
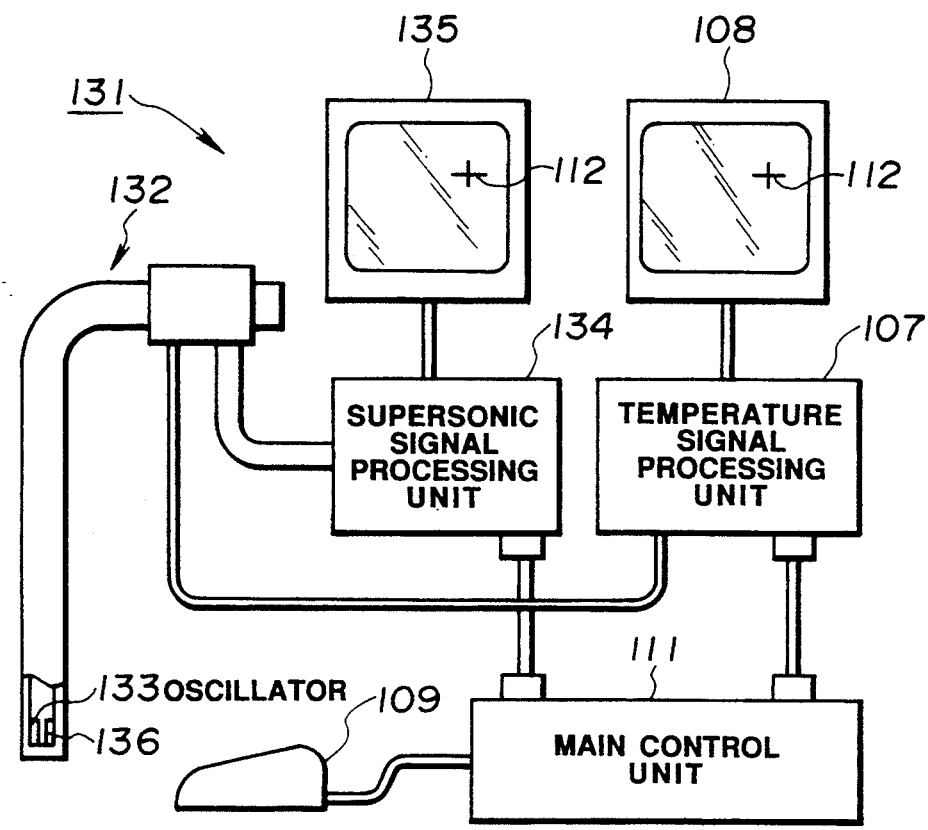
FIGS. 18 to 20 illustrate a fourth embodiment of the present invention, where

FIG. 18 illustrates a medical system 131 with a temperature sensitive function according to a fourth embodiment of the present invention. The system 101 shown in FIG. 15 is arranged in such a manner that a supersonic endoscope (or a supersonic probe) 132 is used in place of the electronic scope 102. A supersonic signal transmitted from a supersonic oscillator 133 included in the supersonic endoscope 132 is processed by a supersonic signal processing unit 134, so that a supersonic tomographic image is displayed on a supersonic image display monitor 135.

The supersonic endoscope 132 has a microstrip antenna 136 serving as a temperature detecting element, the microstrip antenna 136 receiving a microwave so as to transmit it to the temperature signal processing unit 107.

Figure 19:
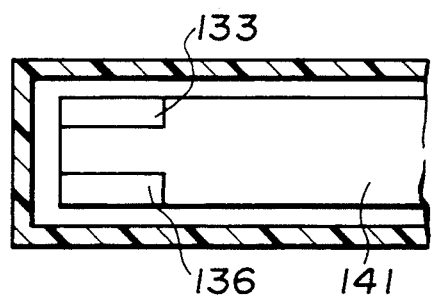
Figure 20:
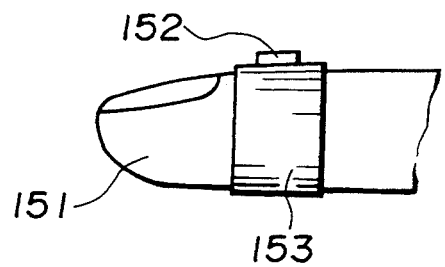

As shown in FIG. 19, the leading portion of the supersonic endoscope 132 is arranged in such a manner that the leading portion of a shaft 141 rotated by a motor (omitted from illustration) has the supersonic oscillator 133 and the microstrip antenna 136 fastened thereto. The supersonic oscillator 133 and the microstrip antenna 136 are rotated in the circumferential direction so as to perform a mecharadial scanning operation. Both the oscillator 133 and the microstrip antenna 136 are covered with rubber or a synthetic resin capable of transmitting the supersonic wave. Furthermore, liquid capable of transmitting the supersonic wave and showing an electrically insulating characteristic is enclosed in their inside portions. The supersonic endoscope 132 according to this embodiment has an endoscope function (omitted from illustration). The other structures are arranged similarly to those of the third embodiment. Also operations and effects resulted are substantially the same as those of the third embodiment.

The fourth embodiment may be modified in such a manner that the mouse 109 is replaced by a structure arranged in such a manner that an annular temperature varying member 153 having a position sensor 152 is fastened to a finger 151. Furthermore, the aforesaid embodiments may be arranged in such a manner that the mouse 109 is replaced by a track ball having a temperature varying member or another pointing device.

Figure 21:
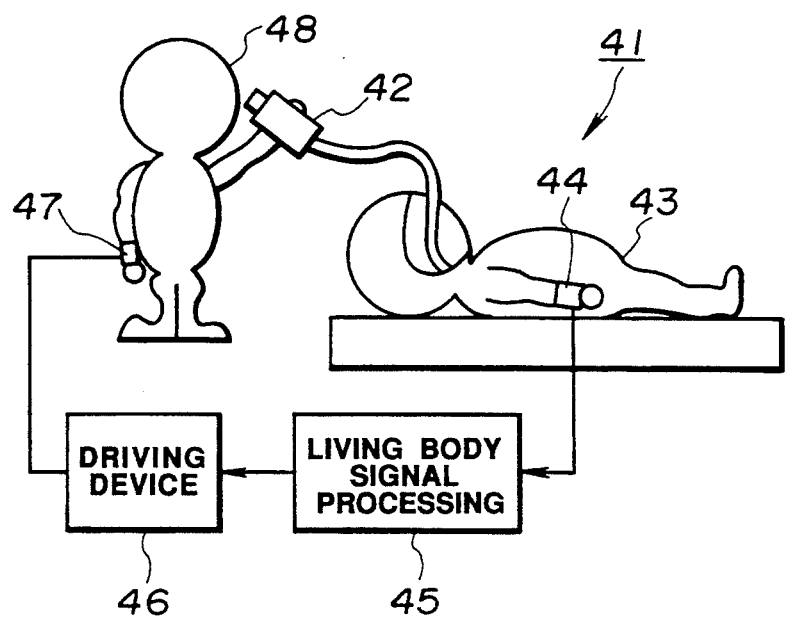

FIG. 21 illustrates a state where a living body information notifying device 41 according to a fifth embodiment of the present invention is used. The device 41 is constituted by an endoscope 42, a living body information detecting section 44 for detecting living body information of a patient 43 observed by the endoscope 42, a living body information signal processing device 45 for processing a signal denoting the living body information detected by the detecting section 44, a driving device 46 for driving the processing device 45 and a stimulus generating section 47 driven by the driving device 46. The stimulus generating section 47 is fastened to an operator 48 who observes the patient 43 through the endoscope 42, so that a stimulus is transmitted to the operator 48. As a result, the living body information of the patient 43 can be reproduced.

Figure 22:
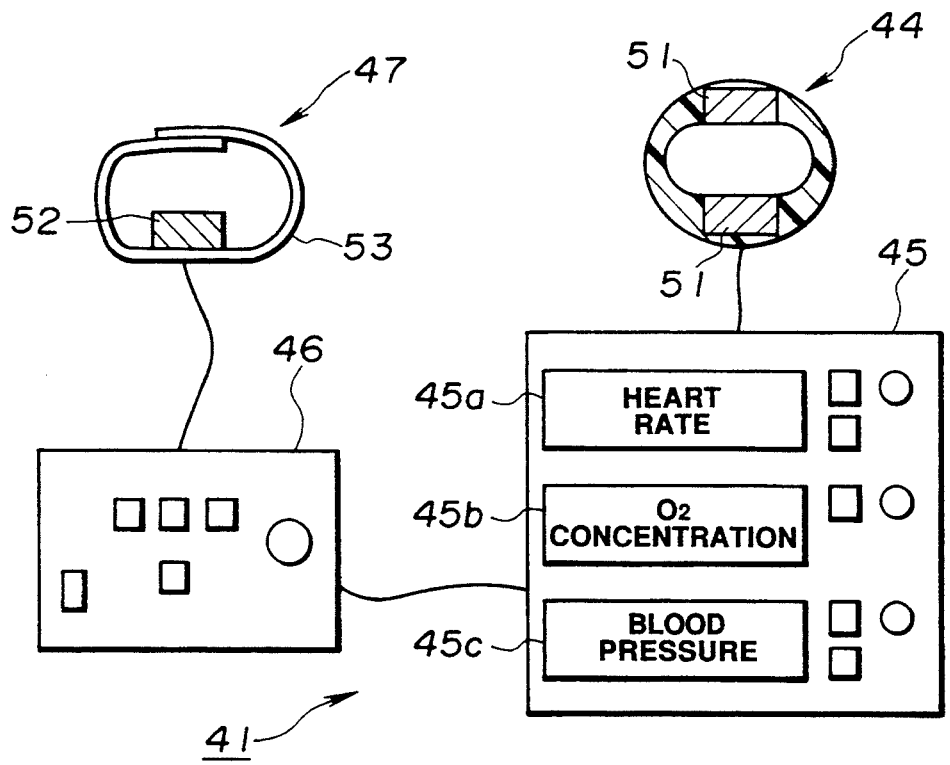

FIG. 22 illustrates the structure of the notifying device 41. The living body information detecting section 44 fastened to the patient 43 is, for example, arranged in such a manner that a living body information detecting element 51 is fastened to a rubber band. The detecting element 51 is able to detect the living body information such as the heart rate, the blood pressure, and the oxygen concentration ($O_2$), and the like of the patient 43. A signal denoting the detected living body information is supplied to the living body information signal processing device 45.

The living body information signal processing device 45 processes the aforesaid signal so as to calculate, for example, the heart rate, the oxygen concentration (content of oxygen), and the blood pressure, and the like. The calculated values are displayed on corresponding display sections 45a, 45b and 45c. The processing device 45 transmits a signal to the driving device 46 as well as displays the values on the display sections 45a, 45b and 45c so as to drive the stimulus generating section 47 via the aforesaid driving device 46. The aforesaid stimulus generating section is constituted in such a manner that a stimulus generating element 52 made of a piezoelectric device or the like is disposed in a fastening band section 53.

FIGS. 23 to 25 illustrate a method of driving the stimulus generating element 52. Heart rate waveforms shown in FIG. 23A are used to drive the stimulus generating element 52 as shown in FIG. 23B disposed below FIG. 23A. As shown in FIGS. 23A and 23B, the stimulus generating element 52 is driven in response to the heartbeat. As a result, the operator is able to confirm the heart rate with the stimulus transmitted from the stimulus generating element 52.

FIGS. 24A and 24B illustrate the relationship between the heartbeat waveform and the quantity of the drive in a case of a high blood pressure and a low blood pressure. If the blood pressure is high, the quantity of the drive of the stimulus generating element 52 becomes large as shown in FIG. 24A. If the blood pressure is low, the quantity of the drive (the amplitude of a driving signal or that of the quantity of the drive) becomes small, as shown in FIG. 24B. Therefore, the blood pressure can be confirmed according to the degree of the quantity of the stimulus.

FIGS. 25A and 25B illustrate the relationship between the concentration of oxygen and the quantity of the drive of the stimulus generating element 52. In a case of FIG. 25A where the concentration of oxygen is low, the oxygen is lacking and therefore driving of the stimulus generating element 52 is commenced in a state where it is expanded. On the other hand, in a case where the concentration of oxygen is low as shown in FIG. 25B, driving of the stimulus generating element 52 is commenced in a state where it is not expanded (it can be confirmed according to the stimulus which clamps the operator 43).

Figure 26:
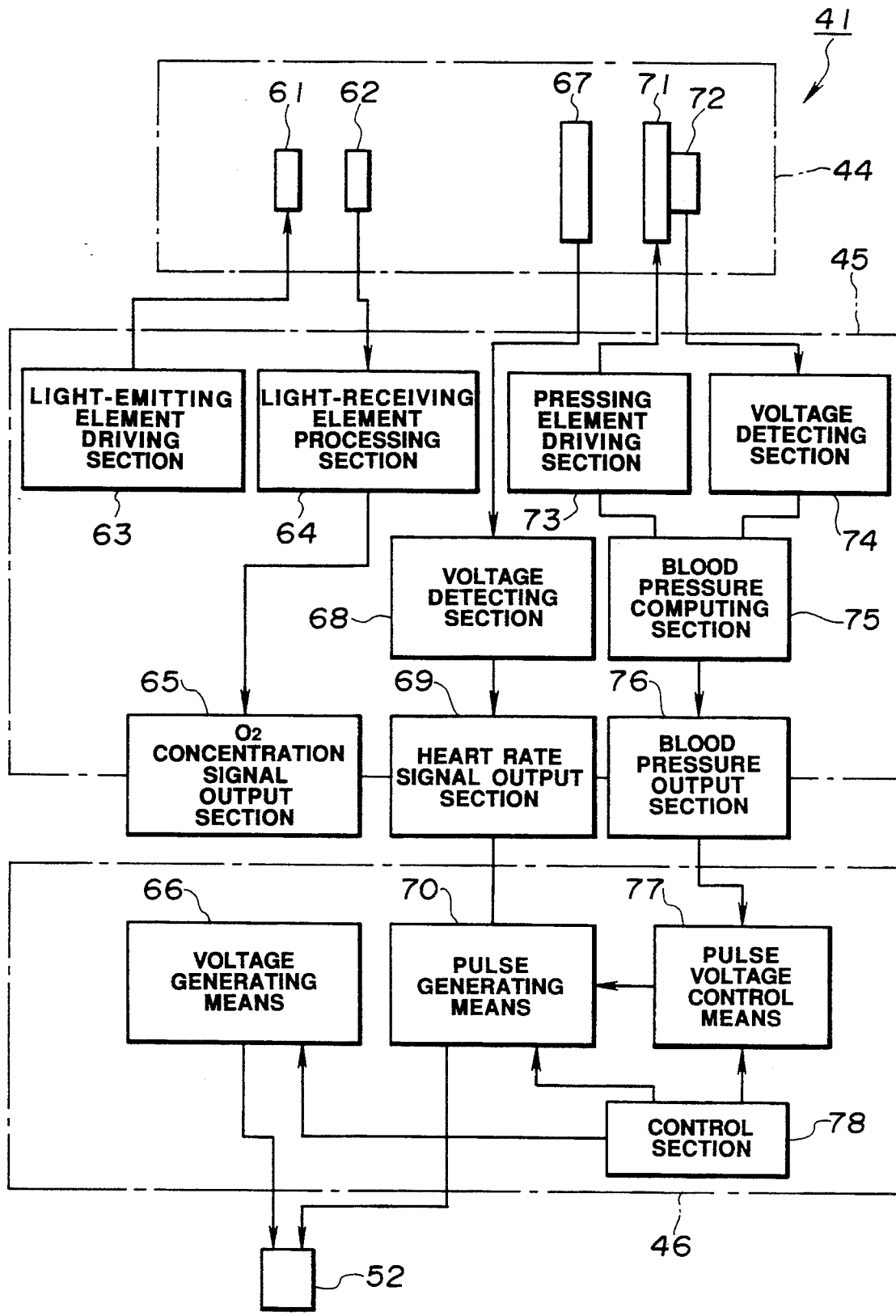

FIG. 26 illustrates the detailed structure of the notifying device 41. The concentration of oxygen is detected by a light-emitting element 61 and a light-receiving element 62. The light-emitting element 61 is driven by a light-emitting element driving section 63. The quantity of light emitted from the light-emitting element 61 and transmitted the living body is detected by the light-receiving element 62 so as to be transmitted to a light-receiving element processing section 64. If the concentration of oxygen is high in this case, the light is dampened considerably. The quantity of damping is used to detect the concentration of oxygen (by, for example, a pulse oxymeter manufactured by Minolta Co., Ltd. or the like).

The aforesaid light-receiving element processing section 64 processes a signal denoting the quantity of light, which has transmitted the living body, so that it is displayed in an oxygen concentration signal output section 65. It is also transmitted to a voltage generating means 66 located in the driving device 46, the voltage generating means 66 using this signal to change the voltage to be always applied to the stimulus generating element 52.

The heartbeat detection is performed in such a manner that the heartbeat is detected by a heartbeat detecting element 67 made of a piezoelectric element or the like and signal denoting this detection is detected by a voltage detecting portion 68. As a result, a signal denoting the heartbeat is displayed by a heartbeat signal output section 69. Furthermore, a pulse generating means 70 is driven in synchronization with the heartbeat signal, causing pulse-like voltage to be applied to the stimulus generating element 52.

The blood detection is performed in such a manner that a blood pressure detecting element 72 is pressed by a pressing element 71. The pressing element 71 is driven by a pressing element driving section 73 and the voltage of a signal detected by the blood pressure detecting element 72 is detected by a voltage detecting portion 74. The voltage is, together with the output from the pressing element driving section 73, supplied to a blood pressure signal computing section 75. The blood pressure signal computing section 75 calculates the blood pressure from the quantity of the drive of the pressing element driving section 73 and the output from the voltage detecting portion 74 so as to transmit information about the blood pressure to a blood pressure signal output section 76.

The blood pressure signal output section 76 acts to display the blood pressure and as well as transmits a signal denoting the blood pressure to a pulse voltage control means 76. The pulse voltage control means 76 controls the voltage level of the pulse output from the pulse generating means 70. Furthermore, the control section 78 controls the quantity of operation of the stimulus generating element 52 and selects (a way in which only one means is driven, a way in which two means are combined, or a way in which three means are combined) the operations of the voltage generating means 66, the pulse generating means 70 and the pulse voltage control means 77 so as to control them.

As the information about the living body, a state of breathing or the like may be detected.

According to this embodiment, the patient 43 can be observed with the endoscope 42. Furthermore, living body information about the patient 43 is detected and is transmitted to the operator as tactile stimulations. Therefore, the operator 43 is able to more specifically recognize the condition of the patient 43, so that the operator 43 is able to obtain information variable to make a diagnosis.

The aforesaid embodiments may be partially combined to constitute another embodiment.

As described above, according to the present invention, the reproduction means is provided in which information about an object is detected by the detecting means and which reproduces the information. As a result, the operator is able to sense the degree and state of the unevenness and the degree of fever by touching the reproduction means. Therefore, the operator is able to perform a palpation by touching the aforesaid reproduction means, enabling the operator to more accurately make a diagnosis as compared to a case in which a diagnosis is made depending only on a visual observation.

Although the invention has been described in its preferred form with a certain degree of particularity, it is understood that the present disclosure of the preferred form has been changed in the details of construction and the combination and arrangement of parts may be resorted to without departing from the spirit and scope of the invention as hereinafter claimed.

What is claimed is:

1. A medical system for diagnosing tactual information from an object which is not capable of being directly palpated, comprising:
   a medical device for visually diagnosing the state of the object;
   detecting means connected to said medical device for detecting three-dimensional information showing the unevenness of the object, further including imaging means for providing a three-dimensional image of a location of the object not normally accessible to direct contact for palpation;
   computing means operably connected to said detecting means for calculating a quantity of unevenness at a predetermined position on said image; and
   object information reproduction means operably connected to said computing means for reproducing said information showing the unevenness of the object at said predetermined position according to an output from said computing means so as to be sensed in a tactile manner by an operator who operates said medical device.

2. A medical system according to claim 1, wherein said object information reproduction means further comprises observing means for enabling the operator to visually observe the state of the object.

3. A medical system according to claim 1, wherein said medical device includes an endoscope device having a function of obtaining an image of the object.

4. A medical system according to claim 3, wherein said object information reproduction means further includes image position instructing means operated by the operator for selecting said predetermined position on said image.

5. A medical system according to claim 4, wherein said image position instructing means further includes a displacement element which can be touched by the hand of the operator and is capable of being displaced at least one dimensionally by a quantity which corresponds to said quantity of unevenness.

6. A medical system according to claim 5, wherein said object information reproduction means includes a magnification means for varying the magnification of the displacement when said displacement element is displaced by a quantity which is in proportion to said quantity of unevenness.

7. A medical system according to claim 3, wherein said endoscope device includes a pair of image pickup means for three-dimensional observation.

8. A medical system according to claim 4, wherein said image position instructing means consists of a mouse.

9. A medical system according to claim 1 further comprising display means for enabling the operator to confirm information of the object according to the output from said detecting means.

* * * * *